(12) United States Patent
Liu et al.

(10) Patent No.: US 7,122,645 B2
(45) Date of Patent: Oct. 17, 2006

(54) DETECTION OF VIABLE AGENTS

(75) Inventors: Haiyan Liu, Collegeville, PA (US); Anthony S. Lubiniecki, King of Prussia, PA (US); Shing H. Mai, Allentown, PA (US); Amy A. Murnane, Audubon, PA (US); Leonard T. Olszewski, Phoenixville, PA (US); Gerardo A. Zapata, Berwyn, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 481 days.

(21) Appl. No.: 10/239,835

(22) PCT Filed: Mar. 27, 2001

(86) PCT No.: PCT/US01/09666

§ 371 (c)(1),
(2), (4) Date: Sep. 25, 2002

(87) PCT Pub. No.: WO01/72964

PCT Pub. Date: Oct. 4, 2001

(65) Prior Publication Data

US 2003/0108864 A1 Jun. 12, 2003

Related U.S. Application Data

(60) Provisional application No. 60/192,226, filed on Mar. 27, 2000, provisional application No. 60/270,316, filed on Feb. 21, 2001.

(51) Int. Cl.
*C12N 15/41* (2006.01)
*C12N 15/40* (2006.01)

(52) U.S. Cl. .................................. 536/23.1; 536/24.32

(58) Field of Classification Search ..................... None
See application file for complete search history.

(56) References Cited

OTHER PUBLICATIONS

Du, et al., "Efficient transduction of human neurons with an adenoassociated virus vector," *Gene Therapy*, vol. 3, No. 3, pp. 254-261 (Mar. 1996).

Erlandsson, et al., "Quantification of Bordetella pertussis in clinical samples by colorimetric detection for competitive PCT products," *APMIS*, vol. 106, No. 11, pp. 1041-1048 (Nov. 1998).

Lipson, et al., "Cell culture-PCR technique for detection of infectious cytomegalovirus in peripheral blood," *J. Clin. Microbiol.* vol. 33, No. 5, pp. 1411-1413 (May 1995).

Reynolds, et al., "Detection of infectious enteroviruses by an integrated cell culture-PCR procedure," *Appl. Environ Microbiol*, vol. 62, No. 4, pp. 1424-1427 (Apr. 1996).

Towers, et al., "One step screening of retroviral producer clones by real time quantitative PCR," *J. Gene Med.*, vol. 1, No. 5, pp. 352-359 (Sep.-Oct. 1999).

Miyagawa et al., "Infection of the Erythroid Cell Line, KU812Ep6 with Human Parvovirus B19 and Its Application to Titration of B19 Infectivity". *J. Virol. Meth.*, 83(1-2): 45-54 (1999).

Fini et al., "Development of Chemiluminescence Competitive PCR for the Detection and Quantification of Parvovirus B19 DNA Using a Microplate Luminometer". *Clin. Chem.*, 45(9): 1391-1396 (1999).

Aubin et al., "Large-Scale Screening for Human Parvovirus B19 DNA by PCR: Application to the Quality Control of Plasma for Fractionation". *Vox Sanguinis*, 78(1): 7-12 (2000).

Gruber et al., "Precise Quantitation of Human Parvovirus B19 DNA in Biological Samples by PCR". *Biologicals*, 26(3): 213-216 (1998).

*Primary Examiner*—James Martinell
(74) *Attorney, Agent, or Firm*—William R. Majarian; Stephen Venetianer; Charles Kinzig

(57) ABSTRACT

A quantitative PCR method has been developed for the simultaneous detection and quantitation of an agent in samples of biologically derived materials. Unlike conventional quantitative PCR detection methods, this assay allows for the detection of viable agents.

1 Claim, 9 Drawing Sheets

Figure 1
Amplification of BVDV genotype I RNA from FBS, AHG 8632 cycle time

Figure 2
Amplification of BVDV genotype II RNA from FBS, AHG 8632

(graph: ?Rn vs cycle time, y-axis from -5.00E-01 to 1.00E+00, x-axis 0 to 40)

Figure 3
Amplification of BVDV genotype II RNA from MDBK cells cultured in medium containing horse serum

Figure 4
Amplification of BVDV genotype II RNA from MDBK cells cultured in medium containing FBS, AHG8632

Figure 5
Amplification of BVDV type II RNA from MDBK cells cultured in medium containing FBS, AGK 7239

Figure 6
Amplification of BVDV genotype I RNA from
MDBK cells grow in the medium containing
10% horse serum

Figure 7
Amplification of BDVD genotype I RNA from
MDBK cells grow in medium spiked with
EBTr cell culture supernatant Amplification of *Mycoplasma argininis* DNA

```
                         SEQUENCE LISTING

<160> NUMBER OF SEQ ID NOS: 17

<210> SEQ ID NO 1
<211> LENGTH: 19
<212> TYPE: DNA
<213> ORGANISM: Bovine Viral Diarrhea Virus

<400> SEQUENCE: 1
cgaaggccga aaagaggct                                                 19

<210> SEQ ID NO 2
<211> LENGTH: 21
<212> TYPE: DNA
<213> ORGANISM: Bovine Viral Diarrhea Virus

<400> SEQUENCE: 2
tcgaaccact gacgactacc c                                              21

<210> SEQ ID NO 3
```

```
-continued

<211> LENGTH: 28
<212> TYPE: DNA
<213> ORGANISM: Bovine Viral Diarrhea Virus

<400> SEQUENCE: 3
ccatccaacg aactcaccac tgttgcta                                        28

<210> SEQ ID NO 4
<211> LENGTH: 19
<212> TYPE: DNA
<213> ORGANISM: Bovine Viral Diarrhea Virus

<400> SEQUENCE: 4
cgaaggccga aaagaggct                                                  19

<210> SEQ ID NO 5
<211> LENGTH: 22
<212> TYPE: DNA
<213> ORGANISM: Bovine Viral Diarrhea Virus

<400> SEQUENCE: 5
gagtgtcgaa ccattgacga ct                                              22

<210> SEQ ID NO 6
<211> LENGTH: 29
<212> TYPE: DNA
<213> ORGANISM: Bovine Viral Diarrhea Virus

<400> SEQUENCE: 6
ttaggccatc caatgaactc actgtaccg                                       29

<210> SEQ ID NO 7
<211> LENGTH: 30
<212> TYPE: DNA
<213> ORGANISM: Bovine Viral Diarrhea Virus

<400> SEQUENCE: 7
ccatccaatg aactcactgc taccgctagt                                      30

<210> SEQ ID NO 8
<211> LENGTH: 18
<212> TYPE: DNA
<213> ORGANISM: Mycoplasma

<400> SEQUENCE: 8
tacacaccgc ccgtcaca                                                   18

<210> SEQ ID NO 9
<211> LENGTH: 24
<212> TYPE: DNA
<213> ORGANISM: Mycoplasma

<400> SEQUENCE: 9
acgttctcgt agggatacct tgtt                                            24

<210> SEQ ID NO 10
<211> LENGTH: 28
<212> TYPE: DNA
<213> ORGANISM: Mycoplasma

<400> SEQUENCE: 10
ccgactttgg gtattaccag ctcccatg                                        28
```

```
<210> SEQ ID NO 11
<211> LENGTH: 33
<212> TYPE: DNA
<213> ORGANISM: Mycoplasma

<400> SEQUENCE: 11
tcatcagtcc taccttagat agttgcctcc gag                          33

<210> SEQ ID NO 12
<211> LENGTH: 29
<212> TYPE: DNA
<213> ORGANISM: Mycoplasma

<400> SEQUENCE: 12
cgacttcacc ccaatcgcta gtcctacct                              29

<210> SEQ ID NO 13
<211> LENGTH: 18
<212> TYPE: DNA
<213> ORGANISM: Mycoplasma

<400> SEQUENCE: 13
tacacaccgc ccgtcaaa                                          18

<210> SEQ ID NO 14
<211> LENGTH: 24
<212> TYPE: DNA
<213> ORGANISM: Mycoplasma

<400> SEQUENCE: 14
acgttctcgt agggtacct tgtt                                    24

<210> SEQ ID NO 15
<211> LENGTH: 28
<212> TYPE: DNA
<213> ORGANISM: Mycoplasma

<400> SEQUENCE: 15
acggttttag atattaccag ctctcata                               28

<210> SEQ ID NO 16
<211> LENGTH: 26
<212> TYPE: DNA
<213> ORGANISM: Mycoplasma

<400> SEQUENCE: 16
cacgaaagtg ggcaataccc aacgcc                                 26

<210> SEQ ID NO 17
<211> LENGTH: 30
<212> TYPE: DNA
<213> ORGANISM: Mycoplasma

<400> SEQUENCE: 17
acgtgttgct aaccattagg aagcgcatgt                             30
```

DETECTION OF VIABLE AGENTS

This is a 371 of International Application PCT/US01/09666, filed Mar. 27, 2001, which claims benefit from the following Provisional Appliations: Ser. No. 60/192,226, filed Mar. 27, 2000 and Ser. No. 60/270,316, filed Feb. 21, 2001.

FIELD OF THE INVENTION

The invention pertains to the detection and quantitation of viable agents in samples to be tested.

BACKGROUND OF THE INVENTION

Traditionally, adventitious agent contamination, viability and infectivity has been investigated using in vitro culture methods, cell culture-based infectivity assays, electron microscopy measurements and more recently DNA-specific polymerase chain reaction ("PCR") methods. Cell culture-based infectivity assays are expensive, time consuming and labor intensive. PCR assays on the other hand are fast, accurate and specific, but currently do not distinguish between "viable" and non-viable adventitious agent contamination. European Patent Publication No. 0 464 010 A describes a polymerase chain reaction protocol for detection of bovine viral diarrhea virus in biological specimens. Likewise, World Patent Publication No. WO 96/36735 describes a rapid method for detection of the presence of a specific mycoplasma in a nucleic acid sample. However, neither of the disclosed methods is able to discriminate between infectious and non-infectious viruses or viable or non-viable mycoplasma, respectively. World Patent Publication No. WO 99/23203 discloses a method for detecting the presence of a virus in a sample. However, as set forth in that publication, the method is restricted to viral detection and requires the use of an immortalized cell line. Moreover, as is the case with the assays described in EP 0 464 010 A and WO 96/36735, the method described in WO 99/23203 is incapable of discriminating between of infectious and non-infectious viruses.

Detection of viability, infectivity and contamination is important in process validation and control of therapeutics such as vaccines and biotechnology products. Testing of cell lines, raw materials and manufacturing processes can greatly benefit from development of fast and reliable means of detecting viable and infectious adventitious agents.

SUMMARY OF THE INVENTION

The instant invention pertains to a method for detecting the presence of a viable agent in a sample comprising a) measuring the amount of a polynucleotide in a sample using a quantitative polymerase chain reaction; b) incubating the sample under conditions that allow for the replication of the agent; c) measuring the amount of the polynucleotide in the sample after the incubation period using a quantitative polymerase chain reaction; and d) comparing the amount of the polynucleotide present in the sample before the incubation period to the amount of the polynucleotide present in the sample after the incubation period wherein an increase in the amount of the polynucleotide indicates the presence of a viable agent in the sample. The polynucleotide to be measured can be DNA or RNA; in the case of RNA, the quantitative polymerase chain reaction is reverse transcriptase polymerase chain reaction ("RT-PCR"). Viable agents that can be detected in the instant method comprise viruses, prokaryotes, yeasts and fungi. Preferred agents that can be detected in the instant method comprise adventitious agents such as parvovirus, polio virus, simian virus 40 (SV40), xenotropic murine leukemia virus (X-MuLV), herpes simplex virus (HSV), minute virus of mice (MVM) and bovine diarrheal virus (BVDV), and prokaryotes of the class Mollicutes. Also preferred are agents gene therapy vectors, including retroviruses, adenoviruses, and adeno-associated viruses. Other preferred agents which may be detected using the instant invention are infectous agents that may be employed as biological weapons, including viral and bacterial agents.

A further embodiment of the instant invention are primers and probes that are useful for the detection of viable agents. These primers and probes may be employed in conventional PCR analyses as well as in the instant method. More specifically, primers and probes for detection of various BVDV types and mycoplasma species are embodied herein.

The instant invention also embodies a test kit for carrying out the instant method, the kit comprising upstream and downstream PCR primers for selectively amplifying a target polynucleotide, and optionally a probe for detecting the amplified target polynucleotide.

BRIEF DESCRIPTION OF THE FIGURES

FIG. 1 presents data from RTqPCR analysis for BVDV type I RNA in gamma-irradiated FBS, lot no. AHG 8632.

FIG. 2 presents data from RTqPCR analysis for BVDV type II RNA in gamma-irradiated FBS, lot no. AHG 8632.

FIG. 3 presents data from RTqPCR analysis for BVDV type II RNA obtained from MDBK cells cultured in medium containing horse serum.

FIG. 4 presents data from RTqPCR analysis for BVDV type II RNA obtained from MDBK cells cultured in medium containing gamma-irradiated FBS, lot no. AHG 8632.

FIG. 5 presents data from RTqPCR analysis for BVDV type II RNA obtained from MDBK cells cultured in medium containing non-irradiated FBS, lot no. AGK 7239.

FIG. 6 presents data from RTqPCR analysis for BVDV type I RNA obtained from MDBK cells cultured in horse serum.

FIG. 7 presents data from RTqPCR analysis for BVDV type I RNA obtained from MDBK cells cultured initially in horse serum, and later exposed to day 4 culture supernate obtained from EBTr cells cultured in horse serum.

DETAILED DESCRIPTION OF THE INVENTION

Figure 8:
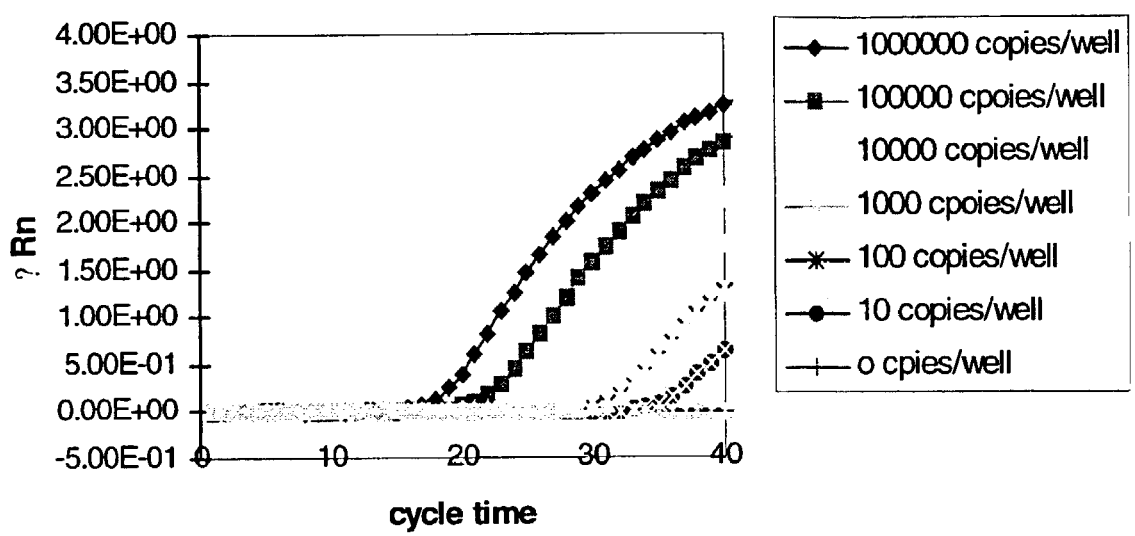
FIG. 8 presents data from qPCR analysis for detection of varying concentrations of DNA obtained from *M. argininis*.

The instant invention essentially comprises a combination of traditional PCR detection methods and a short incubation period to allow for the replication of viable agents present in the sample to be tested. Like traditional PCR detection methods, the instant method is very sensitive and can specifically detect low levels of contamination. However, traditional PCR analysis will detect the presence of a polynucleotide target irrespective of context; i.e., the polynucleotide could be associated with cellular debris left over after sterilization. Traditional PCR is thus unable to discriminate between samples containing viable, replicating agents and those that have been adequately sterilized and/or otherwise inactivated.

The instant invention offers a clear improvement in biotechnology raw material testing and purification process validation. Raw materials, fermentations and purification processes can now be rapidly tested for specific adventitious agent contamination. This method can reduce manufacturing failures by eliminating the practice of proceeding with manufacturing at risk until slow, traditional infectivity assay results are obtained.

For example, manufacturing process validation such as column reuse and chromatographic process limits can benefit from the instant invention. FDA regulations indicate that clearance of viruses and other adventitious agents can be accomplished by two mechanisms. The first mechanism is elimination by filtration or chromatographic separation. The second mechanism is inactivation of infectivity, for example by chemical or temperature inactivation. Traditional cell-based infectivity assays have been used to validate process viral clearance, however these methods are expensive, time consuming, labor intensive and cannot distinguish between removal and inactivation.

Viral clearance studies for chromatographic procedures are performed by spiking the load to the chromatography column with a model virus. The chromatographic procedure is performed and the efficiency of virus removal is determined by measuring the difference between infectious virus particles in the load and effluent. However, when buffers or procedures used in the chromatographic step are capable of inactivating viruses (for example extreme pH, additives such as guanidine HCl, or temperature shifts), the true potential of the chromatographic process to remove viruses is unknown. Inability to determine the absolute potential for virus removal in a process step can lead to manufacturing processes with additional steps solely for the purpose of validating virus clearance. The instant method can be used to facilitate and further enable viral clearance studies in process validation studies such as column reuse and chromatographic process limits. Testing for virus removal and inactivation in such studies is currently impractical due to the numerous sample-testing requirements and the difficulties associated with traditional cell-based infectivity assays. Furthermore since the instant method (like traditional PCR) is highly sensitive and specific, testing for multiple adventitious agents can potentially be performed during a single chromatographic experiment using a cocktail of adventitious model agents such as viruses. Therefore virus infectivity and virus removal can potentially be tested for model viruses in a single chromatographic experiment.

In another embodiment, the instant method can be used to test for infectious replication-competent viruses in therapeutic preparations and to release clinical batches suitable for use in gene therapy. Gene therapy using agents or vectors to introduce therapeutic protein products into patient cells is becoming an important weapon in the arsenal against disease. In this mode of therapy, the product is not a protein or a small chemical entity, but instead a polynucleotide packaged into a viral vector (referred to hereinafter as a gene therapy vector) such as a retrovirus, adenovirus or adeno-associated virus that is capable of delivering the polynucleotide to a target cell. The polynucleotide is introduced into the target cell by the gene therapy vector (referred to hereinafter as transduction), resulting in the intracellular production of a protein with therapeutic benefit.

Some viruses (i.e., retrovirus) that have been engineered for use in gene therapy can integrate their genomes carrying a polynucleotide of interest into the host cell chromosome, potentially producing long term gene expression. Alternatively, viral vectors for use in gene therapy have been developed wherein all or most of their viral genes have been removed and therefore the vectors are replication-defective, yet the vector retains the necessary RNA regions for packaging, reverse transcription and integration. Even though these vectors are replication-defective, the possibility exists that a recombination event can recreate a replication-competent vector (RCV). Testing master cell banks (MCB), working cell banks (WCB), manufacturing process steps, manufacturing lots and therapeutic preparations for RCV is essential to ensure safety. Current testing procedures on MCB, WCB and manufacturing steps for gene therapy vectors are performed in vitro by infection of cell lines permissive of replication-competent viruses. These methods are difficult to perform, time consuming and often difficult to quantitate. The greatest obstacle associated with this type of testing is the long time required to obtain meaningful data, usually on the order of several days. The problem is evident when ex vivo transduced cells need to be tested for RCV immediately before administration. The instant method can therefore be used to monitor for RCV in therapeutic preparations of gene therapy vectors as well as to screen ex vivo transduced cells for RCV prior to administration.

Some gene therapy vectors such as those derived from MuLV are only able to transduce dividing cells, therefore the potency of therapeutic preparations of these vectors can be measured by the instant method. Moreover, since the potency of a therapeutic preparation suitable for use in gene therapy is not necessarily related to the titer of the vector (i.e., the absolute number of vectors), a method of quantifying the transduction capability of a therapeutic preparation is essential as a potency test, as well as a process manufacturing development tool. Similarly adenovirus gene therapy vector preparations need to be free of replication competent adenoviruses. Vector preparations are usually tested on the basis of the ability to form plaques on suitable cell lines such as human lung epithelial cell lines. At best, these systems are time consuming and difficult to implement. The instant method represents a faster, more sensitive technique to evaluate adenovirus vector preparations for the gene therapy.

Although it is possible to make small scale batches of vectors for gene therapy which are free of RCV, it is very difficult to make enough RCV-free virus preparations for large clinical studies or commercial production. This is because the calculated frequency of homologous recombination that may lead to RCA is estimated to be 1 in $10^{12}$. Accordingly, making batches containing $10^{15}$ virus particles free of RCV is a difficult challenge. The instant method can be used test for and quantify RCV in vector preparations and also to screen for production cell lines that are less likely to produce RCV. The instant method can therefore be used as a tool to solve issues of potency, formulation and reproducibility in large scale production.

Adeno-associated virus vectors (AAV) are emerging as a preferred vector for gene therapy. These gene therapy vectors offer several advantages as gene delivery systems. The parental virus does not cause disease, the vectors can transduce both dividing and non-dividing cells, and transduction can persist for the lifetime of the cell. The primary host response that might impact use of AAV vectors is a neutralizing antibody response. Even though Wild-type AAV is not a human pathogen, production of replication competent AAV is to be avoided for several reasons, including the increased likelihood of immune responses to the AAV capsid protein by the treated host, an event that could alter the biology of the vector and reduce potency due to vector elimination. Despite many efforts to reduce replication-competent AAV, it is likely that all transfection systems may have a propensity to generate replication-competent AAV or other recombinations of AAV because it is not possible to eliminate nonhomologous recombination in transfected DNA. Thus, packaging systems in which transfection is avoided may help reduce frequency of recombination.

Standardized assays to analyze and evaluate replication-competent AAV or recombinant species in vector preparations are in development and are not yet universally accepted. The instant method may be used as a tool to detect replication-competent AAV events and evaluate manufacturing of clinical preparations.

The instant method is therefore useful as a general amplification tool capable of detecting replication-competent viruses and retroviruses in vector preparations intended for gene therapy. In addition because the speed of the method and the ability to accurately measure replication, transfection and transduction, the method can be used as an important tool for manufacturing development and product release. In addition, the instant method can provide for rapid testing and monitoring for RCV in treated patients.

In a further embodiment, the instant method may be used for the detection of infectous agents used as biological weapons. Rapid and conclusive analytical tools are an important element in government and public health efforts to detect, deter, and contain the preparation and use of such agents. While a number of methods are currently being developed for this purpose, they all tend to lack one or more of the following critical performance factors: sensitivity, specificity, reproducibility, speed. The instant invention affords the development of assays that overcome some of the shortcomings of other methods by combining the advantages of infectivity assays (showing that the agent is capable of growth, therefore likely to be infectious) and those of PCR assays (showing that the agent is specifically and conclusively what it purports to be, and with high sensitivity), with the advantage of relative assay speed. The combinations of infectivity and PCR methods provides an optimal combination of specificity, sensitivity, and speed.

Samples of interest for testing in such an analytical method include: specimens derived from potential weapons, weapons delivery devices and storage containers, specimens derived from production and/or purification vessels and formulation devices, specimens derived from cell bank containers or inoculum generation containers, specimens derived from environments potentially contaminated with suspected biological weapons, and specimens derived from humans or animals potentially contaminated with suspected biological weapons.

All publications, including but not limited to patents and patent applications, cited in this specification are herein incorporated by reference as if each individual publication were specifically and individually indicated to be incorporated by reference herein as though fully set forth A number of terms shall be utilized in this specification. "Polymerase Chain Reaction" or "PCR" refers to a method of amplifying a specific target polynucleotide through repeated cycles of denaturation of double stranded DNA, annealing of oligonucleotide primers, and DNA polymerization using a thermostable DNA polymerase in the presence of nucleotide triphosphates (see U.S. Pat. Nos. 4,683, 202, 4,683,195 and 4,965,188, each of which is incorporated by reference herein). As used herein, "qPCR" refers to a PCR reaction performed in such a way and under such controlled conditions that the results of the assay are quantitative; i.e., the assay is capable of quantifying the amount of target polynucleotide present in the sample.

The term "reverse transcriptase polymerase chain reaction" or "RT-PCR" refers to a variant of the basic PCR method wherein the starting material is an RNA, which is reverse transcribed into a cDNA prior to PCR (see U.S. Pat. No. 5,262,311, incorporated herein by reference). "RT-qPCR" refers to RT-PCR performed under conditions that afford quantitation of the RNA present in the sample.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

As used herein, an "agent" refers to a biological entity such as a prokaryote, a virus, a yeast and a fungus. A wide array of viable agents can be detected in the instant method. Preferred are single celled organisms, especially prokaryotes, and viruses. Especially preferred are polio virus, simian virus 40 (SV40), xenotropic murine leukemia virus (X-MuLV), herpes simplex virus (HSV), minute virus of mice (MVM) and bovine diarrhea virus (BVDV). Also especially preferred are viral vectors used in gene therapy, including retroviruses, adenoviruses, and adeno-associated viruses. Preferred prokaryotes include members of the class Mollicutes, especially those of the genus Mycoplasma. More preferred are *M. argininis, M. hominis, M. orale, M. salivarium, M. hyorhinis, M. fermentans, M. pirum, A. laidlawii, M. pneumoniae, M. arthritidis, M. hyopneumoniae, M. bovis, M. neurolyticum, M. gallinarum, M. hyosynoviae, M.capricolum, M. pulmonis, M. penetrans, M. genitalium, M. flocculare, M. auris, M. gallopavonis, M. adleriformer, M. pulloruim, M. gallinaceum, M. corogypsi, M. conjunctivae, M. bovirhinis, M. iners, M. edwardii, M. bovoculi, M. ovipneumoniae, M. alkalescens, M. canadense* and *M. synoviae*. Most preferred are *M. argininis, M. hominis, M. orale, M. salivarium, M. hyorhinis, M. fennertans, M. pirum, A. laidlawii, M. pneumoniae* and *M. arthritidis*. Other preferred agents that can be detected are bacterial and viral agents comprising biological weapons. Such viral agents include the viruses associated with smallpox, Ebola, Lassa fever, Eastern, Western and Venezuaelan equine encephalitis, Russian spring-summer/tick borne encephalitis and Yellow Fever. Bacterial agents that comprise biological weapons include *Bacillus anthracis, Brucella suis, Francisella tularensis, Yersinia pestis, Salmonella typhimurium, Salmonella typhi, Shigella species, Vibrio cholera, Yersinia enterocolica* and *Clostridium botulinum*. See also Kortepeter M. G. and Parker G. W. (1999) Potential biological weapons threats, Emerging Infectious Diseases, 5(4): 523-527. It should be noted that other pathogenic organisms exist which are related or unrelated to the above organisms may also be detected by the instant invention. Assays embodying the instant invention are expected to detect on any virus or ricketsia or chiamydia that are propgatable on MRC-5 or VERO cells, and any bacteria propogatable on microbiological media such as BHI agar.

As used herein, an "adventitious agent" refers to a biological agent present in a sample that is not normally found in that sample under aseptic conditions. Adventitious agents, as used herein, are considered contaminants whose reduction, elimination or neutralization is desirable.

As used herein, the term "viable" refers to the ability of an agent to carry out those biochemical and genetic processes, including gene expression (i.e., transcription), and DNA and RNA replication, that allow the agent to propagate under suitable conditions. For purposes of the instant specification, agents that require the presence of a host cell in order to propagate are considered to be "viable" so long as they are capable of propagation in the presence of a suitable host cell. Moreover, for agents such as viruses and certain mycoplasma, viability necessarily connotes infectivity; i.e., without the ability to infect a compatible host cell, such agents would be consider non-viable. Thus, the instant method may be used to detect infectious adventitious agents.

The instant method relies on the exquisite sensitivity of PCR to detect low levels of a specific target polynucleotide that is synthesized as part of the replicative cycle of an adventitious agent present in a sample. The assay will only be positive if there is a net increase in the quantity of the target polynucleotide after some suitable period of incubation under conditions that allow for growth and replication of the adventitious agent. Accordingly, even in samples containing the target polynucleotide, if the quantity of that polynucleotide does not increase after a suitable incubation period as a consequence of replication of the contaminating adventitious agent, the assay will be scored as negative. Thus the instant method is distinguished from standard PCR or RT-PCR methods that statically measure the quantity of a polynucleotide in a given sample.

The instant method also offers an advantage over standard PCR or RT-PCR methods in that the incubation period can lead to increased ability to detect low levels of contamination. Normally, the volume of sample which is tested by PCR is limited to 1 to 20 microliters. Thus if a sample contains a low level of an adventitious agent, the sample which is tested by PCR may fail to contain even one cell or particle of the agent. The incubation step, however, affords the opportunity to begin with a larger volume of the test article and increase the level of adventitious agent to the point where even a very small volume is likely to contain a detectable level.

The skilled artisan will choose the target polynucleotide based on its association with the agent to be detected. Selection of an appropriate polynucleotide target will also depend on the level of specificity or cross-reactivity desired. That is, the target polynucleotide may be species- or isolate-specific, thereby affording specific detection of agents at the species or isolate level, or may be less specific, thereby affording the simultaneous detection of a broader class of agents at the level of the genus or higher. It is well within the skill in this art to choose target polynucleotides and corresponding PCR primers that are appropriate for the level of detection and specificity desired.

Moreover, multiple, unrelated agents, especially adventitious agents, can be detected simultaneously even where there is no significant sequence homology between the target polynucleotides. This may be accomplished by "multiplexing" the PCR steps of the method by inclusion of additional sets of PCR primers, each specific for a unique target polynucleotide. One skilled in this art will chose target polynucleotides and corresponding PCR primers so as to maximize compatibility in a multiplexed assay format.

Any sample that is suspected of containing a viable agent may be tested in the method. One skilled in the art will appreciate that certain samples may require pretreatments, such as dilution, buffering, extraction, filtration and the like, prior to carrying out the instant method. For the detection of adventitious agents, preferred are samples derived from biological materials including animal- and plant-derived materials such as blood and blood products, sera, tissues, tissue extracts, cells and cellular extracts, and materials given off or otherwise excreted or eliminated by an animal or plant. These materials may include clinical specimens, as well as raw materials and supplies used in industrial or other processes that require minimal adventitious agent contamination. Also preferred are samples comprising preparations of biological materials in various states of purity as may be derived from in-process sampling during preparation and purification.

Quantitation of the specific target polynucleotide is accomplished by performing PCR under appropriate conditions and measuring, either directly or indirectly, the production of amplified copies of the target polynucleotide. An especially useful method to quantify the target polynucleotide is by use of the TaqMan® assay (PE Biosystems, Foster City, Calif.; see also U.S. Pat. No. 5,210,015, incorporated herein by reference). However, any method that allows detection and quantitation of amplified products that are produced as a result of performing the polymerase chain reaction on a specific polynucleotide target is suitable for use in the instant assay. Examples of other such methods include quantitative competitive PCR or PCR followed by gel electrophoresis with direct quantitation of the amplicon band in the gel by densitometry.

A key step of the instant method that distinguishes it from the prior art and affords detection of viable agents is the incubation step wherein an agent that is present in the sample to be tested is allowed to grow, divide, and if necessary, infect target cells (as in the case of viruses and certain mycoplasma), resulting in the production of additional copies of the target polynucleotide. Incubation conditions will vary with the nature of the agent to be detected and with the nutritional and environmental requirements of the host cell line. For example, if the agent is a virus, incubation conditions will be suitable for the maintenance of cell lines that will support propagation of the virus. Media formulation, temperature, oxygen and $CO_2$ concentration, etc. can be determined empirically. Alternatively, cell lines that support the growth of many viruses are well known, as are appropriate cell culture conditions. Likewise, media and conditions to support the growth of prokaryotes, yeast and fungal contaminants are well known in this art.

EXAMPLES

The present invention will now be described with reference to the following specific, non-limiting examples.

Example 1

Detection of Infectious Viral Contaminant in Cells and Fetal Bovine Serum

Bovine viral diarrhea virus, or BVDV, is a member of the genus Pestivirus within the family Flaviviridae. The pestivirus genome consists of a single-stranded nonpolyadenylated RNA molecule, with a size of about 12.5 kb (Collett, M. S.

et al. (1988) *Virology* 165:191-199; Deng, R. and K. Brock. (1992) *Virology* 191: 867-879; Meyers, G. et al. (1989) Virology 171:555-5674; Moormann, R. M. et al. (1990) *Virology* 177:184-198). BVDV is one of the most important viral pathogens of cattle. Mild symptoms of the disease include transient fever, leukopenia, and rapid recovery; however, the severe acute disease is marked by high fever, watery diarrhea and occasional death (Perdrizet, J. A. et al. (1987) *Cornell Vet* 77:46-74; Brownlie, J. et al. (1987) *Ann Rech Vet* 18:157-166). Approximately 50 to 90% of cattle are found to be infected by BVDV in the United States (Baker, J. C. (1987) *J. Am Vet Med Assoc* 190: 1449-1458; Ernst, P. B. et al. (1983) *Compend Contin Educ Pract Vet* 5:S581-S589).

Fetal bovine serum (FBS) is used widely in the culture of cell lines. Unfortunately, fetal bovine serum purchased from vendors is often contaminated by BVDV through BVDV-infected cattle. Two genotypes of BVDV are grouped by Ridpath et. al., BVDV I and BVDV II (Ridpath, J. F. et al. (1994) *Virology* 205:66-74). These two genotypes are classified based on the comparison of sequences from the 5' untranslated region (UTR) of the viral genome. Several RT-PCR methods have been published for the detection of BVDV (Lewis, T. L. et al. (1991) *Arch Virol.* 117:269-278; Letellier, C. et al. (1999) *Vet. Microbiology* 64:155-167; El-Kholy, A. A. et al. (1998) *Revue Scientifique et Technique* 17(3):733-742) based on the knowledge of gene sequences. However, although these RT-PCR methods have great assay sensitivity, it can not determine if the viral RNA measured is from infectious or non-infectious virus.

Materials and Methods

Materials

TaqMan® Gold RT-PCR Kit and TaqMan® PCR universal master mix were obtained from PE Biosystems. RNAeasy® mini kit and QIAamp® viral RNA mini kit were obtained from Qiagen. Various fetal bovine sera were purchased from GIBCO, ATCC, Hyclone, and JRH.

Viruses, Cell Lines

NY-1 BVDV and other BVDV isolates were obtained from Cornell Diagnostic. BT (Bovine Turbinate, cat. no. ATCC CRL1390), EBTr (embryonic trachea, Bovine, *Bos taurus,* cat. no. ATCC CCL 44), and MDBK (Bovine Kidney cell, *Bos taurus,* cat. no. ATCC CCL 22) cell lines were purchased from American Type Culture Collection (ATCC).

Primer/Probe Sets Designed for BVDV

Two primer/probe sets for the detection of type I and type II BVDV were designed using TaqMan® Primer Express software. These are listed in Table 1. One forward primer (FP), one reverse primer (RP), and one probe were used for the detection of type I BVDV. This same forward primer, a different reverse primer, and two other probes were used for the detection of type II BVDV.

TABLE 1

| BVDV Genotype | | Primer/probe combinations (5'-3') | |
|---|---|---|---|
| Type I | Forward | CGA AGG CCG AAA AGA GGC T | (SEQ ID NO:1) |
| | Reverse | TCG AAC CAC TGA CGA CTA CCC | (SEQ ID NO:2) |
| | Probe | CCA TCC AAG GAA CTC ACC AGT GTT GCT A | (SEQ ID NO:3) |

TABLE 1-continued

| BVDV Genotype | | Primer/probe combinations (5'-3') | |
|---|---|---|---|
| Type II | Forward | CGA AGG CCG AAA AGA GGG T | (SEQ ID NO:4) |
| | Reverse | GAG TGT CGA ACC ATT GAC GAC T | (SEQ ID NO:5) |
| | Probe 1 | TTA GGC CAT CCA ATG AAC TCA CTG TAC GG | (SEQ ID NO:6) |
| | Probe 2 | CCA TCC AAT GAA CTC ACT GCT ACC GCT AGT | (SEQ ID NO:7) |

Quantitative Real-Time PCR (QPCR) Reaction

The qPCR reaction mixture contained 900 nM primers (both forward and reverse) and 200 nM probe. The activation of Taq polymerase was 95° C. for 10 minutes followed by forty cycles of denaturation at 95° C. for 15 seconds and annealing and elongation at 60° C. for 1 minute. A total qPCR assay time is 2 hours. The amplicon length of genotype I is 122 bps (from position 87-207; see GenBank Accession No. AF091605) and the amplicon length of genotype II is 127 bp (from position 87 to 213; see GenBank Accession No. AF039175). These amplicons are within the 5' UTR region. The total RT-qPCR assay required six hours.

Isolation of RNA and Transcription of RNA to cDNA from Cells and Supernatant

RNeasy® mini kit was used to isolate RNA from cells. QIAamp® viral RNA mini kit was used to isolate RNA from cell culture supernatant. TaqMan® Gold RT-PCR Kit was then used for the transcription of RNA to cDNA. The procedures for the isolation of RNA and the transcription of RNA to cDNA were described in instructions included in these kits. The qPCR was then performed using ABI Prism 7700 Sequence Detection System.

Determination of BVDV RNA in FBS

RNA was isolated from FBS using QIAamp® viral RNA Mini kit. A total of 2 uL of RNA was then used for reverse transcription. After reverse transcription, a total of 10 uL of cDNA was subjected to qPCR assay.

Cell Culture for the BVDV Infectivity Study

MDBK cells were seeded at $5 \times 10^4$ to $1 \times 10^5$ cells/mL in 5 mL MEM Earles w/glutamine medium containing 10% horse serum in a T25 flask. Cells were then incubated overnight at 37° C., in an atmosphere of 5% $CO_2$ in air. After incubation, fresh medium containing 10% of test FBS was used to replace the previous medium. Cells were then incubated for an additional 1 to 4 days or up to 6 passages (cells were passed every four days). One flask of cells was trypsinized each day, and cells were resuspended into 5 mL serum free medium. One mL of this cell suspension was centrifuged at 9000 rpm for 5 minutes. RNA was then extracted from the cell pellet by RNeasy® Mini kit. RT-qPCR assay was performed as described in the section above to determine the amount of BVDV in the sample.

Cell culture for the Evaluation of RT-qPCR Assay for the Detection of Viable BVDV Contamination in Cell Line EBTr cell line was purchased from ATCC. Cells were grown in MEM Earles w/glutamine medium containing 10% horse serum. In order to determine if this cell line was infected with BVDV, a total of 100 uL of a day 4 culture supernatant was spiked into BVDV free cells, MDBK cell line, which were grown in the same type of medium. MDBK cells grown in the 10% horse serum medium without spiking were used as a control. Cells were harvested at 0, 8, 24, and 48 hours. One mL of cell suspension was processed and subjected to RT-qPCR assay as described above.

Results and Discussion

Evaluation of the RT-QPCR Assay for the Detection of the Presence/Absence of BVDV in Serum Gamma-irradiated FBS, AHG 8632 and non-gamma irradiated FBS, AGK 7239 from Hyclone were tested by RT-qPCR assay to determine if BVDV was present in the serum lots. The amplification of BVDV RNA by RT-qPCR suggests that both type I (FIG. 1) and type II (FIG. 2) BVDV RNA are found in gamma-irradiated FBS, AHG 8632. The non-gamma irradiated FBS, AGK 7239, was also found to be contaminated with both type I and type II BVDV RNA (data not shown).

Evaluation of RT-qPCR Assay for the Detection of Infectious and Non-Infectious BVDV in Serum-Containing Medium In order to understand if sera AHG 8632 and AGK 7239 contained infectious BVDV or non- infectious BVDV RNA (including inactivated BVDV), BVDV-uninfected MDBK cells were first grown in media containing either of these two sera. Medium containing horse serum was used as a control. MDBK cells were cultured for up to 6 passages (p6). According to the instant assay, no type II BVDV viral RNA was found in MDBK cells when these cells were grown in either horse serum (FIG. 3) or gamma-irradiated FBS (AHG 8632, FIG. 4)-*containing* media even after 6 passages. It was concluded that no infectious type II BVDV was present in these two sera. However, type II BVDV was detected in MDBK cells grown in medium containing non-gamma irradiated FBS, AGK 7239, as shown in FIG. 5. The BVDV titer increased with length of cell culture from day 0 to day 4. Type I BVDV was also found in MDBK cells when cells were cultured in medium containing non-gamma irradiated FBS, AGK 7239, but not in gamma-irradiated FBS, AHG 8632 (data not shown). All these data suggest that non-gamma irradiated FBS, AGK 7239 contained both infectious type I and type II BVDVs. Gamma-irradiated FBS, AHG 8632 contained both type I and type II BVDV RNA, but not infectious BVDV.

Evaluation of the RT-QPCR Assay for the Detection of Infectious BVDV in EBTr Cell Line EBTr cell line was grown in medium containing 10% horse serum. This day 4 culture supernatant was then spiked into BVDV-uninfected MDBK cells grown in the medium containing 10% serum in order to see if EBTr cells are contaminated with infectious BVDV. MDBK cells grown in 10% horse serum medium without spiking were used as a control. Cells were harvested at various hours and subjected to the RT-qPCR assay. No viral RNA was detected even after 48 hours in the control MDBK cells (FIG. 6) since no RNA amplification was found by RT-qPCR. However, in the MDBK culture spiked with EBTr supernatant (FIG. 7), viral RNA was detected at 8, 24, and 48 hours, with an increase of Type I BVDV RNA titers during incubation from 0 to 48 hours. These data suggest that EBTr cells were infected by type I BVDV. Similar results for this cell line were also found for type II BVDV (data not shown). We conclude that the EBTr cell line was not only infected by infectious type I BVDV, but also infected by infectious type II BVDV.

Investigation of BVDV Contamination in FBS Purchased from Various Vendors

Ten different fetal bovine sera (FBS) from various sources were tested by RT-qPCR assay to evaluate if any of these sera were contaminated with infectious BVDV. Two BVDV uninfected cell lines, MDBK and BT, were used in this study. Results are shown in Table 2.

TABLE 2

| Vendor | Catalog No. | Lot No. | BVDV detected in MDBK cells | BT cells |
|---|---|---|---|---|
| GIBCO USA | 26140-087 | 1022442 | − | − |
| GIBCO Mexico | 10437-010 | 1021468 | − | − |
| ATCC | 30-2020 | AHC 7863 | − | − |
| Hyclone (40 nm filtered) | SH30070.03 | AGK 7239 | + | + |
| | SH30070.01 | AHG 8632 (· −irradiated) | − | − |
| Hyclone Australia (3 × 0.1 um filtered) | SH30084.01 | AGH 8631 | − | − |
| | | AHG 8631 (· −irradiated) | − | − |
| Hyclone (3 × 0.1 um filtered) | SH30088.01 | AGK 7212 | − | − |
| | | AGK 7212 (· −irradiated) | − | − |
| JRH | 12107-78p | 8B2031 (· −irradiated) | − | − |

The data obtained from both BT cells and MDBK cells agree that one of those ten FBS lots, lot no. AGK 7239 obtained from Hyclone, was contaminated with infectious BVDV even though this lot of serum was filtered through a 40 nm filter. No infectious BVDV was found in the other nine FBS lots purchased. Some of these FBS were treated with gamma irradiation and some were not. It was found that not all non-gamma irradiated serum was contaminated with BVDV.

Example 2

Detection of Infectious Mycoplasma Contaminant

The instant assay may be used for the detection and quantitation of mycoplasma contamination in cell culture.

Materials and Methods

Materials

TaqMan® PCR universal master mix was obtained from PE Biosystems. TA cloning kit was purchased from Clone Tech. DNAzol® was obtained from GIBCO BRL (cat. no. 10503)

Mycoplasma Species:

All the mycoplasma species were purchased from ATCC.

Primer/probe sets designed for detection of Mycoplasma:

Several primer/probe sets were designed for the detection of mycoplasma contamination in cell culture using Taq-Man® Primer Express software. These are listed in Table 3. Each primer/probe set includes one forward primer (FP), one reverse primer (RP), and three probes. The entire length of qPCR product is 127 bps. The Set I primers and Probes I-1 and I-2 are derived from the sequence set forth in GenBank Accession No. X58556. Probe I-1 was useful for the detection of the majority of mycoplasma species, whereas Probe I-2 detected *M. neurolyticuin,* and Probe I-3 (derived from the sequence set forth in GenBank Accession No. AF232909) detected *M. capricolum.* The Set II primers and Probe II-3 were derived from the sequence set forth in GenBank Accession No. AF132740. Probe II-1 was derived from the sequence set forth in GenBank Accession No. M23940, and Probe II-2 was derived from the sequence set forth in GenBank Accession No. M23932. Probe II-1 detected *M. pirum,* whereas Probe II-2 detected *A. laidlawii,* and Probe II-3 detected *M. pneumoniae.*

TABLE 3

| Primer Set | | Primer/probe combinations (5' to 3') | |
|---|---|---|---|
| Set I | Forward | TAC ACA CGG CCC GTC ACA | (SEQ ID NO:8) |
| | Reverse | ACG TTC TCG TAG GGA TAC CTT GTT | (SEQ ID NO:9) |
| | Probe I-1 | CCGACTTTGGGTATTACC AGCTCCCATG | (SEQ ID NO:10) |
| | Probe I-2 | TCA TCA GTC GTA GCT TAG ATA GTT GCC TCG GAG | (SEQ ID NO:11) |
| | Probe I-3 | CGACTTCACCCCAATCGC TAGTCCTACCT | (SEQ ID NO:12) |
| Set II | Forward | TAC ACA CGG CCC GTC AAA | (SEQ ID NO:13) |
| | Reverse | ACG TTC TCG TAG GGG TAG CTT GTT | (SEQ ID NO:14) |
| | Probe II-1 | ACGGTTTTAGATATTACC AGCTCTCATA | (SEQ ID NO:15) |
| | Probe II-2 | CAC GAA AGT GGG CAA TAC CCA ACG CC | (SEQ ID NO:16) |
| | Probe II-3 | ACGTGTTGCTAACCATT AGGAAGCGCATGT | (SEQ ID NO:17) |

Preparation of Purified DNA from Mycoplasma Species for DNA Standard

Lyophilized mycoplasma culture from various species were purchased from ATCC. To each lyophilized culture tube was added I mL DNAzol®. After centrifugation, the supernate was withdrawn and 0.5 mL of absolute ethanol was added to precipitate DNA. Following a second centrifugation, the DNA pellet was washed with 95% ethanol. After air drying, the DNA pellet was dissolved in sterilized irrigation water. The concentration of DNA was measured by PicoGreen assay. The genomic DNA copy number was then determined.

Isolation and Extraction of DNA from Cell Culture

DNAzol® was used for the isolation and extraction of DNA from samples. A total of 100 uL of test sample comprising a mixture of culture supernate and cells was added to 1 mL DNAzol® and gently mixed. Following centrifugation to a maximum speed for 10 minutes, 1 mL of supernate was transferred to a fresh tube to which was added 0.5 mL of 100% ethanol. After centrifugation for 10 minutes at maximum speed, the resulting DNA pellet was washed twice with 95% ethanol. The extracted DNA pellet was air dried and resuspended in 20 uL of sterile irrigation grade water.

Quantitative Real-Time PCR (QPCR) Reaction

ABI Prism 7700 Sequence Detection System (TaqMan®) was used for the qPCR assay. A total reaction volume of 25 uL contained 10 uL of extracted DNA sample (template), TaqMan® universal master mix, 300 nM of each primer and 100 nM of probe. The activation of Taq polymerase proceeded at 95° C. for 10 minutes and was followed by forty cycles of denaturation at 95° C. for 15 seconds and annealing and elongation at 60° C. for 1 minutes. The total qPCR assay time was approximately 2 hours.

Results and Discussion

Sensitivity of qPCR Assay for the Detection of Mycoplasma

In order to determine the sensitivity of qPCR assay for the detection of mycoplasm, DNA from *M. argininis* at various concentrations (i.e., $10^1$, $10^2$, $10^3$, $10^4$, $10^5$, $10^6$, $10^7$ genomic copies) was subjected to qPCR assay using the Set I primers and Probe I-1 described above. The results are shown in FIG. 8. It is evident that qPCR assay using the primers described herein can detect mycoplasma species at 10 less genome copies. Similar results were also found from all other mycoplasma species listed in the Table 4 (see below).

Identification of Mycoplasma Species by QPCR Method

A total of thirty five mycoplasma species were detected in the qPCR assay using some combination of primers and probes described above (see Table 4). Set I primers with probe I-1 detected the majority of mycoplasma species purchased from ATCC (a total of 30 of 35 mycoplasma species was detected). Set I primers and probe 1-2 detected *M. neurolyticum* and probe 1-3 detected *M. capricolum. M. purium, A. laidlawii,* and *M. pneumnoniae* can be detected by set II primers/probe II-1, set II primers/probe II-2, and set II primers/probe II-3, respectively. These three mycoplasma species are included in ten most common mycoplasma seen as contaminants in cell culture. The other seven most common mycoplasma species seen in contaminated cell cultures (i.e., *M. argininis, M. hominis, M. orale, M. salivarium, M. arthriditis, M. hyorhinis,* and *M. fermentans*) can be detected by using set I primers and probe I-1.

TABLE 4

| Mycoplasma species | Primer Set (FP/RP) | Probe |
|---|---|---|
| M. argininis | I/I | I-1 |
| M. hominis | I/I | I-1 |
| M. orale | I/I | I-1 |
| M. salivarium | I/I | I-1 |
| M. hyorhinis | I/I | I-1 |
| M. fermentans | I/I | I-1 |
| M. pirum | II/II | II-1 |
| A. laidlawii | II/II | II-2 |
| M. pneumoniae | II/II | II-3 |
| M. arthritidis | I/I | I-1 |
| M. hyopneumoniae | I/I | I-1 |
| M. bovis | I/I | I-1 |
| M. neurolyticum | I/I | I-2 |
| M. gallinarum | I/I | I-1 |
| M. hyosynoviae | I/I | I-1 |
| M. capricolum | I/I | I-3 |
| M. pulmonis | I/I | I-1 |
| M. penetrans | I/I | I-1 |
| M. genitalium | I/I | I-1 |
| M. flocculare | I/I | I-1 |
| M. auris | I/I | I-1 |
| M. gallopavonis | I/I | I-1 |
| M. adleriformer | I/I | I-1 |
| M. pullorum | I/I | I-1 |
| M. gallinaceum | I/I | I-1 |
| M. corogypsi | I/I | I-1 |
| M. conjunctivae | I/I | I-1 |
| M. bovirhinis | I/I | I-1 |
| M. iners | I/I | I-1 |
| M. edwardii | I/I | I-1 |
| M. bovoculi | I/I | I-1 |
| M. ovipneumoniae | I/I | I-1 |
| M. alkalescens | I/I | I-1 |
| M. canadense | I/I | I-1 |
| M. synoviae | I/I | I-1 |

Quantitation of Mycoplasma Contamination in Cell Culture by gPCR

Figure 9:
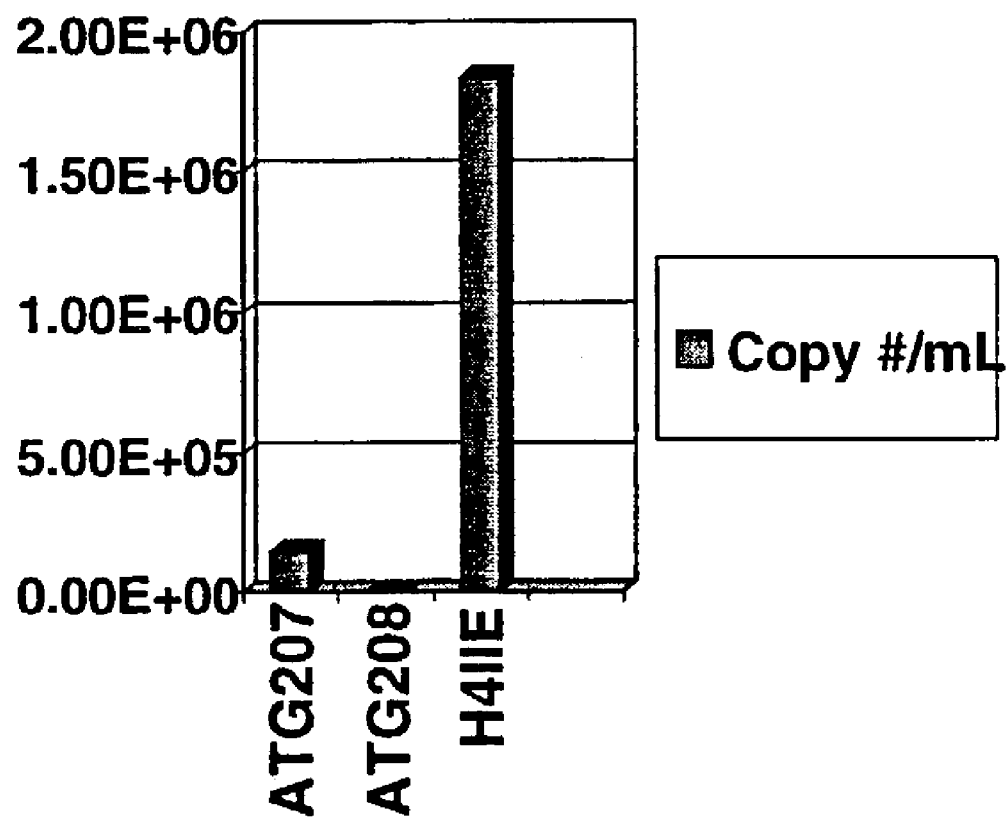
FIG. 9 presents data from qPCR analysis of mycoplasma contamination of cultured ATG207, ATG208 and H4IIE cells.

Cell culture from three cell lines, ATG207, ATG208, and H4IIE were assayed for mycoplasma contamination by qPCR. The results were shown in FIG. 9. These results indicate that no mycoplasma contamination was found in ATG208; however, $1.46 \times 10^5$ and $1.84 \times 10^6$ genome copies per mL were measured in ATG207 and H4IIE, respectively.

Example 3

Detection of Agents Useful for Biological Weapons

Detection of Viruses

Most viruses that infect humans are capable of replication in MRC-5 and/or VERO cells. Samples suspected of containing potential viruses can be prepared for cultivation in MRC-5 and VERO cells by filtration through a 0.2 micrometer filter, and inoculated aseptically into replicate cell cultures in the presence of antibiotics such as penicillin and gentamycin to reduce the likelihood of bacterial contamination, and fungizone to reduce the likelihood of fungal contamination. A portion of the inoculum is reserved for subsequent PCR testing. One or more of the replicate cultures is sampled soon after inoculation (within one hour) for subsequent PCR testing After 18-30 hours of incubation at 35-37.5° C., a sample can be withdrawn from the incubated inoculated cell cultures for PCR analysis.

PCR testing is done with the original prepared sample, the zero incubation time sample, and the one day incubation time sample. After a suitable number of rounds of PCR amplification, the reaction product should be probed in parallel with a series labeled nucleic acid probes encoding specific gene sequences from viruses of interest as possible biological weapon agents. A positive result is observed as a substantial increase in the amount of PCR reaction product in the incubated sample with respect to the zero time control or the original sample. The identity of the infectious agent can be determined from which probe of the panel of probes reacts specifically with the incubated PCR reaction product. It should be noted that if recombinant DNA technology was utilized to create a novel hybrid infectious agent, that more than one probe might be specifically positive. Thus, a positive result can be obtained in about one day from sample processing.

Detection of Bacteria

Many bacteria can readily be cultivated on specialized microbial media for isolation and propagation of pathogenic microbes, such as Brain-Heart Infusion (BHI) agar. Samples can be processed for aseptic inoculation by suspending in sterile phosphate buffered saline (PBS), and spread across a potion of the surface of the agar plate. A portion of the inoculum is reserved for subsequent PCR testing and stored under refrigerated conditions. After reflaming the spreader, or obtaining a sterile spreader, the partially spread inoculum is further spread across another protion of the agar surface. This process is repeated a total of 4-6 times until substantial dilution of the inoculum is obtained, and growth of any organinsms present is likely to result in well-isolated colonies After incubation for about 24 hours at 35-37.5° C. in a humid 5% $CO_2$ aerobic environment or in an anaerobic Brewer jar environment, well isolated colonies are picked aseptically, and a portion is subjected to PCR analysis as described above. It is recognized that an initial enrichment step of about one day's incubation at 35-37.5° C. in a specialized medium for the propagation of pathogens such as BHI broth prior to initiation of plating on BHI agar may be advantageous.

PCR testing is done with the original prepared sample and the one day incubation time sample After a suitable number of rounds of PCR amplification, the reaction product should be probed in parallel with a series labeled nucleic acid probes encoding specific gene sequences from bacteria of interest as possible biological weapon agents. A positive result is observed as a substantial increase in the amount of PCR reaction product in the incubated sample with respect to the original sample The identity of the infectious agent can be determined from which probe of the panel of probes reacts specifically with the incubated PCR reaction product. It should be noted that if recombinant DNA technology was utilized to create a novel hybrid infectious agent, that more than one probe might be specifically positive. Thus, a positive result can be obtained in about one day from sample processing.

What is claimed is:

1. An isolated polynucleotide consisting of the nucleotide sequence set forth in SEQ ID NO:1 or the complement thereof.

* * * * *